US011309075B2

(12) United States Patent
Anthony et al.

(10) Patent No.: US 11,309,075 B2
(45) Date of Patent: Apr. 19, 2022

(54) GENERATION OF A TRANSACTION SET

(71) Applicant: Cerner Innovation, Inc., Kansas City, KS (US)

(72) Inventors: Leo P. Anthony, Phoenixville, PA (US); Kathleen M. Collins, Coatesville, PA (US); Asheesh Nadkarni, Lansdale, PA (US); Jaqulin N. Maria Sebastian, Malvern, PA (US); Hiral Shah, Ellicott City, MD (US)

(73) Assignee: Cerner Innovation, Inc., North Kansas City, MO (US)

( * ) Notice: Subject to any disclaimer, the term of this patent is extended or adjusted under 35 U.S.C. 154(b) by 863 days.

(21) Appl. No.: 15/393,671

(22) Filed: Dec. 29, 2016

(65) Prior Publication Data
US 2018/0189450 A1    Jul. 5, 2018

(51) Int. Cl.
*G16H 40/20* (2018.01)
*G06F 16/25* (2019.01)

(52) U.S. Cl.
CPC ............. *G16H 40/20* (2018.01); *G06F 16/25* (2019.01)

(58) Field of Classification Search
CPC ............................... G16H 40/20; G06F 16/25
USPC ........................................................... 705/2
See application file for complete search history.

(56) References Cited

U.S. PATENT DOCUMENTS

| 4,491,725 A | 1/1985 | Pritchard |
| 4,667,292 A | 5/1987 | Mohlenbrock et al. |
| 4,852,000 A | 7/1989 | Webb et al. |
| 4,857,716 A | 8/1989 | Gombrich et al. |
| 4,858,121 A | 8/1989 | Barber et al. |
| 5,018,067 A | 5/1991 | Mohlenbrock et al. |
| 5,077,666 A | 12/1991 | Brimm et al. |
| 5,121,945 A | 6/1992 | Thomson et al. |
| 5,191,522 A | 3/1993 | Bosco et al. |
| 5,253,164 A | 10/1993 | Holloway |
| 5,301,105 A | 4/1994 | Cummings |

(Continued)

FOREIGN PATENT DOCUMENTS

JP    11161704    6/1999

OTHER PUBLICATIONS

Yang et al., "Selecting Structural Patterns for Classification", Proceedings of the 38th Hawaii International Conference on System Sciences—2005.

(Continued)

*Primary Examiner* — Robert A Sorey
*Assistant Examiner* — Kimberly A. Sass
(74) *Attorney, Agent, or Firm* — Shook, Hardy & Bacon LLP

(57) ABSTRACT

Systems and methods are provided to electronically generate an Electronic Data Interchange (EDI) 835 transmission to test 835 processing systems. EDI 835 transmissions include vast amounts of data that are input into the transmission in a unique way. If even one space is off, the 835 transmission will not be correctly processed and may be kicked back by the system. This has serious consequences as it may result in incorrect or non-recording of a payment on a claim. Unfortunately, most systems are not tested for 835 processing capabilities before going live due to the time intensive nature of generating 835 transmissions for testing. The present application describes an innovative way to electronically generate 835 transmissions.

19 Claims, 16 Drawing Sheets

(56) References Cited

U.S. PATENT DOCUMENTS

| | | |
|---|---|---|
| 5,307,262 A | 4/1994 | Ertel |
| 5,325,293 A | 6/1994 | Dorne |
| 5,359,509 A | 10/1994 | Little et al. |
| 5,517,405 A | 5/1996 | McAndrew et al. |
| 5,550,734 A | 8/1996 | Tarter et al. |
| 5,557,514 A | 9/1996 | Seare et al. |
| 5,704,044 A | 12/1997 | Tarter et al. |
| 5,704,347 A | 1/1998 | Schlobohm |
| 5,752,234 A | 5/1998 | Withers |
| 5,772,585 A | 6/1998 | Lavin et al. |
| 5,790,674 A | 8/1998 | Houvener et al. |
| 5,819,228 A | 10/1998 | Spiro |
| 5,835,897 A | 11/1998 | Dang |
| 5,867,821 A | 2/1999 | Ballantyne et al. |
| 5,915,241 A | 6/1999 | Giannini |
| 5,924,074 A | 7/1999 | Evans |
| 5,933,809 A | 8/1999 | Hunt et al. |
| 5,950,169 A | 9/1999 | Borghesi et al. |
| 5,956,689 A | 9/1999 | Everhart |
| 5,974,389 A | 10/1999 | Clark et al. |
| 5,991,733 A | 11/1999 | Aleia et al. |
| 6,182,070 B1 | 1/2001 | Megiddo et al. |
| 6,189,005 B1 | 2/2001 | Chakrabarti et al. |
| 6,208,973 B1 | 3/2001 | Boyer et al. |
| 6,263,330 B1 | 7/2001 | Bessette |
| 6,282,531 B1 | 8/2001 | Haughton et al. |
| 6,317,783 B1 | 11/2001 | Freishtat et al. |
| 6,336,139 B1 | 1/2002 | Feridun et al. |
| 6,341,265 B1 | 1/2002 | Provost et al. |
| 6,343,271 B1 | 1/2002 | Peterson et al. |
| 6,345,288 B1 | 2/2002 | Reed et al. |
| 7,006,893 B2 | 2/2006 | Hart et al. |
| 7,013,284 B2 | 3/2006 | Guyan et al. |
| 7,072,842 B2 | 7/2006 | Provost et al. |
| 7,127,456 B1 | 10/2006 | Brown et al. |
| 7,392,471 B1 | 6/2008 | Ford et al. |
| 7,404,140 B2 | 7/2008 | O'Rourke |
| 7,797,172 B2 | 9/2010 | Fitzgerald |
| 7,801,744 B2 | 9/2010 | Patterson |
| 7,831,442 B1 | 11/2010 | Chappel |
| 7,870,009 B2 | 1/2011 | Patterson |
| 7,881,950 B2 | 2/2011 | Patterson |
| 7,937,653 B2 * | 5/2011 | Dejean ............... G06F 17/2745 715/234 |
| 7,970,629 B2 | 6/2011 | Christen |
| 8,050,945 B2 | 11/2011 | Patterson |
| 8,738,396 B2 * | 5/2014 | Green, III ............ G06F 19/328 705/2 |
| 9,058,352 B2 | 6/2015 | Dudala |
| 9,721,315 B2 | 8/2017 | Christen |
| 2001/0034618 A1 | 10/2001 | Kessler et al. |
| 2001/0037224 A1 | 11/2001 | Eldridge et al. |
| 2001/0054155 A1 | 12/2001 | Hagan et al. |
| 2002/0004727 A1 | 1/2002 | Knaus et al. |
| 2002/0010597 A1 | 1/2002 | Mayer et al. |
| 2002/0019754 A1 | 2/2002 | Peterson et al. |
| 2002/0032583 A1 | 3/2002 | Joao |
| 2002/0032584 A1 | 3/2002 | Doctor et al. |
| 2002/0035488 A1 | 3/2002 | Aquila et al. |
| 2002/0120473 A1 | 8/2002 | Wiggins |
| 2002/0133503 A1 | 9/2002 | Amar et al. |
| 2002/0147867 A1 | 10/2002 | Satlow |
| 2002/0198741 A1 | 12/2002 | Randazzo |
| 2003/0014280 A1 | 1/2003 | Jilinskaia et al. |
| 2003/0018496 A1 | 1/2003 | Hambright et al. |
| 2003/0050804 A1 | 3/2003 | Hendershot |
| 2003/0055679 A1 | 3/2003 | Soll et al. |
| 2003/0069760 A1 | 4/2003 | Gelber |
| 2003/0083906 A1 | 5/2003 | Howell et al. |
| 2003/0149594 A1 | 8/2003 | Beazley et al. |
| 2003/0158760 A1 | 8/2003 | Kannenberg |
| 2003/0191665 A1 | 10/2003 | Fitzgerald et al. |
| 2003/0191667 A1 | 10/2003 | Fitzgerald |
| 2003/0191669 A1 | 10/2003 | Fitzgerald et al. |
| 2003/0208379 A1 | 11/2003 | Haskey et al. |
| 2003/0216831 A1 | 11/2003 | Hart et al. |
| 2003/0229516 A1 | 12/2003 | Nickerson |
| 2004/0078228 A1 | 4/2004 | Fitzgerald et al. |
| 2004/0153336 A1 | 8/2004 | Virdee et al. |
| 2005/0010452 A1 | 1/2005 | Lusen |
| 2005/0010863 A1 | 1/2005 | Zernik |
| 2005/0033609 A1 | 2/2005 | Yang |
| 2005/0137912 A1 | 6/2005 | Rao |
| 2005/0216315 A1 | 9/2005 | Anderson |
| 2006/0041487 A1 | 2/2006 | Santalo et al. |
| 2006/0080142 A1 | 4/2006 | Hart |
| 2006/0149784 A1 | 7/2006 | Tholl et al. |
| 2006/0150107 A1 | 7/2006 | Leung et al. |
| 2008/0027759 A1 | 1/2008 | Flam et al. |
| 2008/0126346 A1 * | 5/2008 | Zheng ................... G16H 40/67 |
| 2009/0018866 A1 | 1/2009 | Christen |
| 2010/0145734 A1 * | 6/2010 | Becerra ............... G06Q 10/087 705/4 |
| 2010/0174558 A1 | 7/2010 | Smith et al. |
| 2013/0006683 A1 * | 1/2013 | Rao ....................... G06Q 10/06 705/7.11 |
| 2014/0058757 A1 | 2/2014 | Patterson |
| 2014/0108043 A1 | 4/2014 | Ach et al. |
| 2014/0278579 A1 | 9/2014 | Mojahed |
| 2015/0127375 A1 | 5/2015 | Hwang et al. |
| 2017/0329910 A1 * | 11/2017 | Selwanes ............... G16H 10/60 |

OTHER PUBLICATIONS deVois, Inc., "Claims Administration", printed from website on Sep. 20, 2002 http://www.denovis.com/product/claims.htm.

* cited by examiner

```
Hospital ABCD - Notepad

ISA*00*          *00*          *ZZ*000000000609      *ZZ*33T057       *030717*0700*};*00501*007003000*1*P*>~
GS*HP*000000000021*33T057*20160527*0700*3368*X*005010X221A1~
ST*835*165155~
BPR*I*34.44*C*ACH*CCP*01*044000037*DA*063226190045*1444555789***01*021300077*DA*109901111*20160527~
TRN*1*E1*20160527146437112153983*1444555789~
REF*F2*4A.01~
DTM*405*20160525~                                        102
N1*PR*Tricare~
N3*666 TTTTT AAA~
N4*NNN NNNN*PA*19355~
PER*BL~
N1*PE*Gold Hospital*XX*20150S0118~
N3*RRRRRRRRRRRRR RRRR*999 SSSSS MMMMMM BBBBBBB~
N4*AAAAAA*PA*19355~
REF*TJ*33T057~
LX*1~                                105
CLP*5556790001*1*289*231.2*17.34*12*20160527014524*11*1~
NM1*QC*1*Scenario1*Remit1****HN*915823316~
MOA***MA01*MA18~
REF*EA*11041924~
DTM*232*20160301~
DTM*233*20160301~
AMT*AU*248.54~
SVC*NU>0110*50*40**1~           ⎫
DTM*472*20160301~                ⎬ 104a
CAS*CO*45*7~                     ⎭
AMT*BY*43~
LQ*HE*N28~
LQ*HE*N48~
DTM*472*20160301~                ⎫
CAS*CO*45*16.8~                  ⎬ 104b
CAS*PR*1*4.8**2*2.4~             ⎭
AMT*B6*103.2~
LQ*HE*N28~
LQ*HE*N48~
SVC*NU>0259*119*95.2**1~
DTM*472*20160301~
```

Remittance Processing Rules

Home | Help | Logoff

Home Page

Master File Central

Remittance Processing Rules — Remittance Processing Rules

| Rule Sets | Active |
|---|---|
| 04/11/2016 | |
| 08/04/2008 - 08/04/2008 | |
| 08/04/2008 - 09/23/2008 | |
| 09/23/2008 - 10/24/2008 | |
| 10/24/2008 - 12/05/2008 | |
| 12/05/2008 - 09/03/2009 | |
| 09/22/2009 - 10/08/2009 | |
| 10/08/2009 - 03/16/2010 | |
| 03/16/2010 - 07/06/2010 | |
| 07/06/2010 - 07/16/2010 | |
| 07/19/2010 - 08/04/2010 | |
| 08/06/2010 - 08/09/2010 | |
| 08/09/2010 - 08/09/2010 | |
| 08/20/2010 - 09/06/2010 | |
| 09/06/2010 - 10/29/2010 | |
| 10/29/2010 - 03/02/2011 | |
| 03/02/2011 - 03/04/2011 | |
| 03/04/2011 - 03/31/2011 | |
| 04/11/2011 - 05/31/2011 | |
| 06/01/2011 - 06/02/2011 | |
| 06/03/2011 - 09/14/2012 | |

(1301 brace on rule sets list)

Manage List

Rule Set: 04/11/2016

Start date: 04/11/2016  Start time: 05:17 AM
Stop date: /  /          Stop time:
Description: 4.2 Remit Testing-50
Comment: DO NOT CHANGE ANY RULES THEY ARE SET UP FOR 4.2 REMIT TESTING!

Rules

A rule set must contain at least one rule.

[Add/Copy]  [View]  [Delete]

| Seq | Rule Name |
|---|---|
| 2 | Testing Remit Attribute |
| 3 | Remit Procedure Code = 99214 or 99211 |
| 4 | Remit Procedure Code = 90801 or 35331 or 81003; Use DenMgt |
| 5 | Part Provider Dawson and RemitProcCd NE 90801 |
| 6 | Part Provider = GoldHosp, SVC BUR, Remit ProcCd 97001 or 99201 |
| 7 | Participating Provider = Vanderwallet, Irvinged O |

Testing Remit Attribute Details

Expression: "10148" IN [aRemittanceProcessingRuleCriteria.remitProcedureCode] AND
aRemittanceProcessingRuleCriteria.participatingProvider EQ "Narrow Ridge General" AND
aRemittanceProcessingRuleCriteria.participatingProvider EQ "Bertuzzi, Jeffery C" AND
aRemittanceProcessingRuleCriteria.businessOfficeShortName EQ "Rolling Narrow BO" AND
aRemittanceProcessingRuleCriteria.claimPayerRank EQ 1

(1302 brace on expression)

```
Hospital ABCD - Notepad

LX*1~
CLP*5563830010101*1*6000*351.2*1129.76*12*20160603032434*11*1~
NM1*QC*1*S3 L TC  222*PAT****HN*32432~
MIA*0****MA01~
REF*EA*11042820~
DTM*232*20160401~
DTM*233*20160405~
AMT*AU*1480.96~
SVC*NU>0110*1500*87.75**1~
DTM*472*20160401~
CAS*CO*45*1129.8~
CAS*PR*2*282.45~
AMT*B6*370.2~
LQ*HE*N34~
SVC*NU>0110*1500*87.75**1~
DTM*472*20160402~
CAS*CO*45*1129.8~
CAS*PR*2*282.45~
AMT*B6*370.2~
LQ*HE*N34~
SVC*NU>0110*1500*87.75**1~
DTM*472*20160403~
CAS*CO*45*1129.8~
CAS*PR*2*282.45~
AMT*B6*370.2~
LQ*HE*N34~
SVC*NU>0110*1500*87.95**1~
DTM*472*20160404~
```

GENERATION OF A TRANSACTION SET

BACKGROUND

The Electronic Data Interchange Healthcare Claim Transaction set (EDI 837) is utilized to submit medical claim billing information, encounter information, or both. It can be sent from providers of services to payers, either directly or via intermediary billers and claims clearinghouses. Payers respond to the EDI 837 with an EDI Healthcare Claim Payment/Advice Transaction set (EDI 835). The EDI 835 is used to make payments, send Explanation of Benefits (EOB), send Explanation of Payment (EOP) remittance advice, and the like. The EDI 835 is used to detail payments of a claim including what charges were paid, reduced or denied; whether there was a deductible, co-insurance, co-pay, etc.; any bundling or splitting of claims or line items; how the payment was made; and the like.

The computer-to-computer exchange of this information calls for a specific format to be used in EDI 837 and EDI 835 generation. Because of this standardized requirement, senders and recipients of EDI 837 and EDI 835 forms must be able to process the forms quickly and efficiently. Various providers have created programs to facilitate such processing. However, testing of the runtime environment usually does not occur with respect to the 835 processing. This is because payers do not provide test cases for 835 claims and generating the 835 forms needed to test the system is a massive undertaking that is extremely time intensive and impractical. Additionally, the 835 processing systems need to be able to handle extremely large files that are sometimes too large for a given system.

Furthermore, the percentage of error is enormous with manual generation of 835 forms. Thus, testing of 835 processing of systems is typically not performed, which leads to live implementations of systems that have errors related to 835 processing that must be dealt with after a live implementation and, consequently, after the error has already been made with actual data.

SUMMARY

Embodiments of the present invention relate to, among other things, automated generation of 835 forms. The automated generation may be utilized for testing systems before they are implemented in a live environment. At a high level, the tool automatically generates the 835 forms and can extract information from various sources (e.g., client specific databases, user input and 837 transmissions, etc.) and assemble an 835 form in the correct format in a matter of minutes.

Accordingly, in one aspect, an embodiment of the present invention is directed to one or more computer storage media storing computer-useable instructions that, when executed by a computing device, cause the computing device to perform operations. The operations include detecting an indication of a database to use to generate an EDI 835 transmission (hereinafter "835 transmission"); extracting claims data from the database; detecting test data to include in the 835 transmission; and electronically generating one or more 835 transmissions corresponding to the claims data and the test data.

In another embodiment, an aspect is directed to a computer-implemented method for generating a user interface for an application. The method includes detecting a selection of a database to use for electronic generation of an 835 transmission; extracting, from the database, claims information from a first claim and claims information from a second claim; generating a first 835 transmission using the claims information from the first claim; generating a second 835 transmission using the claims information from the second claim; merging the first 835 transmission and the second 835 transmission; generating a merged 835 transmission including claims information for both the first 835 transmission and the second 835 transmission.

A further embodiment is directed to a computer system comprising: one or more processors; and one or more computer storage media storing computer-useable instructions that, when used by the one or more processors, cause the one or more processors to: detect a selection of a database to use for electronic generation of an 835 transmission; extract, from the database, claims information from a first claim and claims information from a second claim; generate a first 835 transmission using the claims information from the first claim; generate a second 835 transmission using the claims information from the second claim; merge the first 835 transmission and the second 835 transmission; generate a merged 835 transmission including claims information for both the first 835 transmission and the second 835 transmission.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein:

FIGS. 1-15 are exemplary screenshots illustrating an 835 generation tool being used to electronically generate 835 transmissions in accordance with some implementations of the present disclosure.

DETAILED DESCRIPTION

Figure 2:
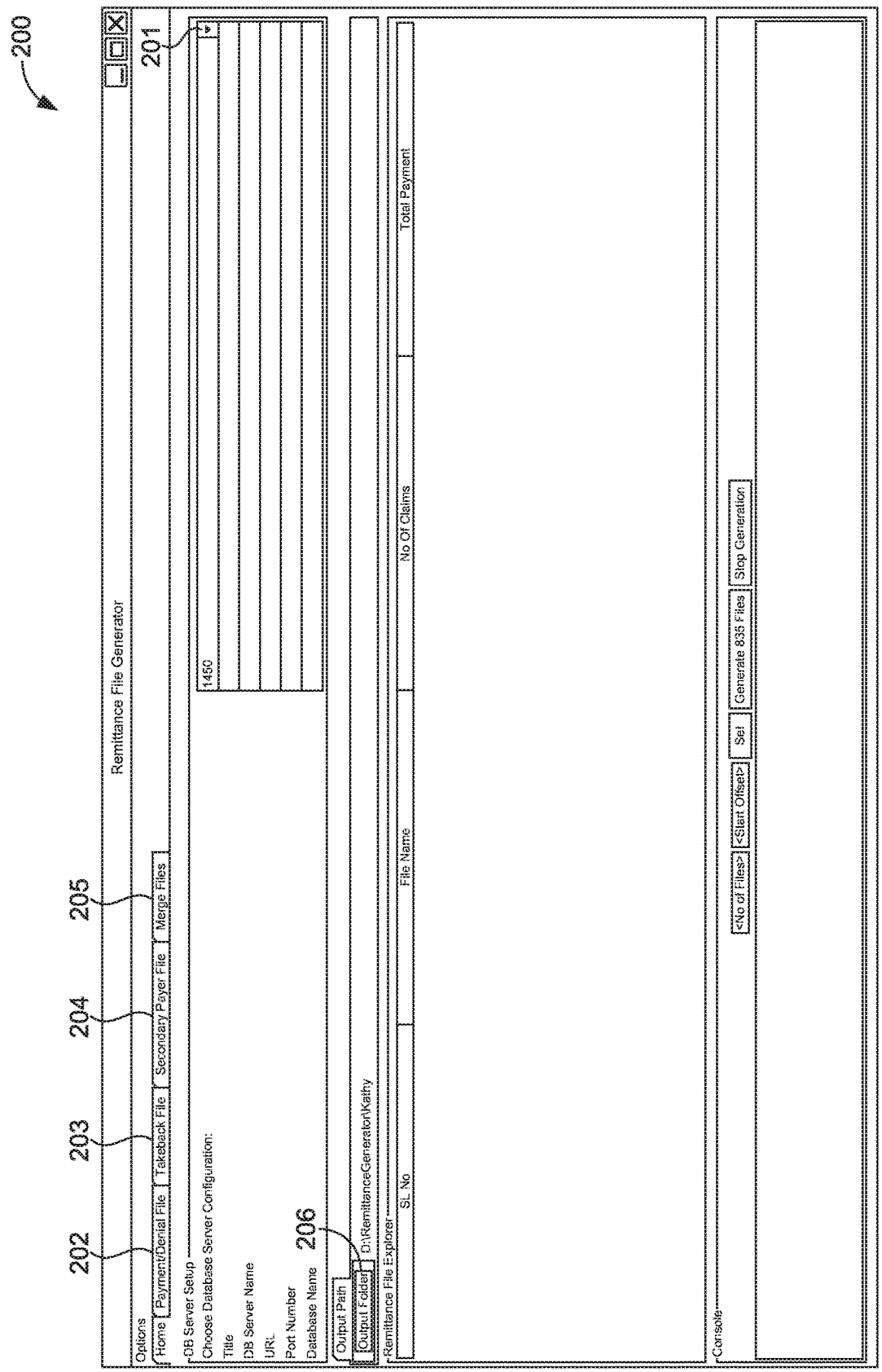

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide electronic generation of 835 transmissions utilizing generated claims. An 835 transmission generator of the present disclosure utilizes generated claims found in one or more databases to electronically generate 835 transmissions for system testing before implementation. The one or more databases may be separate from the processor including the 835 transmission generator. The one or more databases may be associated with an entity different than the entity associated with the 835 transmission generator.

The 835 transmission generator can evaluate the one or more databases to identify what claims have been generated. The information from the generated claims ("claims information") may be used to populate 835 transmissions. The types of data extracted can include claims tables and master files that include payer information, payer name, patient name, services rendered with charges, expected reimbursements, dates of service, providers, etc.

The 835 transmissions may be supplemented with test data used, for example, to test rules that pertain to 835 transmissions. For example, test data that specifically tests rules written for the system may be input into the 835 transmissions to test specific rules to make sure they are performing correctly. Different rules may be desired for 835 transmissions from different entities. Thus, the tool provides a way to test several different rules applied to 835 transmissions such that 835 transmissions from several different entities are processed correctly.

Typically, users do not test systems for 835 transmission processing performance prior to live implementation of the system simply because the generation of 835 transmissions is too time consuming and test cases for 835 claims is not something provided by payers. However, once live implementation occurs without testing, problems may be detected that could have been caught during testing. For example, a transmission did not transfer the residual balance to the next coordinating party, but the entity of the system wanted it to transfer or vice versa. Transmissions may be lost altogether or rejected. Once processed with an error or rejected, the processing is done. Rules may be changed to handle the transmissions going forward, but it is not easy to clean up the already-made mess. For instance, a rejected transmission is rejected and won't be reprocessed. Thus, it could take weeks to correct the error in processing since it will have to be corrected via manual efforts (e.g., telephone calls to other entities such as insurance companies to correct the error). The tool solves these problems by generating hundreds of remittances (or even more) that mirror what will come back from payers in little time at all.

Additionally, 835 files have been increasing in size to sizes too large to handle by 835 processing systems. The 835 transmission generator of the present invention can create test files that are extremely large in size to test the size capabilities of the system. This provides insight into what the system can handle and also in potential areas to increase scalability in order to increase the processing power of the system.

By way of example to illustrate, FIGS. 1-15 are screenshots showing electronic generation of an 835 transmission in accordance with an embodiment of the present invention. In particular, the screenshots of FIGS. 1-15 provide an example in which an 835 transmission is generated to test one or more rules of an 835 transmission processing system.

FIG. 1 is an exemplary 835 transmission data set 100. The data set 100 includes an amount remitted 101 and a provider 102. Lines 103*a*, 103*b*, and 103*c* are summed to total an amount while also taking into account lines 104*a* and 104*b*. That number is reflected at value 105. Additional information may be included in 835 transmissions including, but not limited to, services rendered and codes corresponding thereto, remittance response codes, payer indicator, payee indicator, patient name, charge information, date of service, and the like. If generated by hand, the 835 transmission would need to be replicated exactly as it appears—every asterisk, every space, every single character shown in FIG. 1 is necessary for successful processing of an 835 transmission of the represented generated claim. Furthermore, there are hundreds and hundreds of codes to choose from in the generation of the forms (e.g., any codes that are within the lists maintained by the National Uniform Claim Committee listing and the Centers for Medicare and Medicaid Services). This is a massive undertaking that is not easily accomplished.

The 835 transmission generator of the present disclosure can extract the data from all necessary sources and format it such that it complies with the 835 transmission format standards. Thus, the 835 transmission generator can electronically generate the 835 transmission, including data from one or more sources, format the data, and create a unique header for each generated 835 transmission.

Initially, a database, or any other source, may be selected from which to extract claims information. FIG. 2 provides an exemplary interface 200 illustrating this feature. The source list 201 is provided and may be expanded via a drop down menu (as shown in menu 301 of FIG. 3). Additionally, a type of transmission may be selected via options 202, 203, 204, and 205. A payment/denial file may be generated via option 202. A takeback file may be generated via option 203. A secondary payer file may be generated via option 204. Finally, multiple files may be merged via option 205 (as discussed in further detail below). An output indicator 206 may also be provided to designate where the output should be stored. For instance, a user may want to generate a plurality of 835 transmissions to utilize for testing a system and may wish to keep each generated 835 transmission saved in the same location.

As previously mentioned, the database selected may be associated with the same or a different entity than the entity associated with the 835 transmission generator. The database may include an electronic medical record database comprising a plurality of electronic medical records of patients. The database may include claims that have already been submitted for reimbursement. By using actual claims data, the generated 835 transmission for testing will be more reliable.

Figure 3:
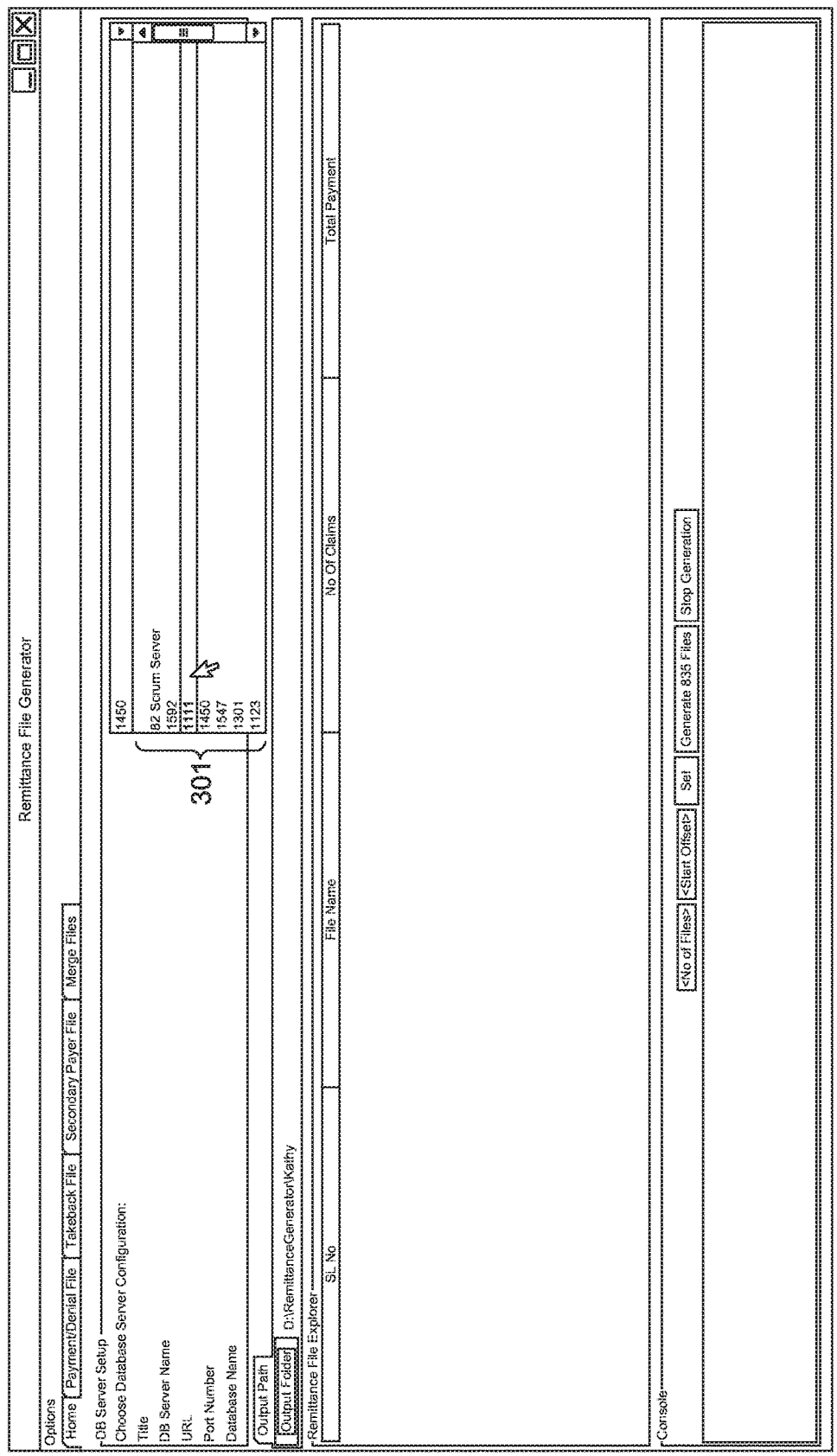

FIG. 3 provides an exemplary interface 300 for selecting the source from which to extract claims information. The drop down menu 301 may be expanded and any source therein may be selected. Exemplary sources may include data stores including claims information. An entity testing their system may, for instance, configure their data store to link with the 835 transmission generator. Other entities' data stores may also be linked such as payers, for instance. Alternatively, the 835 transmission generator may use an actual claim file to create the 835 transmission.

Figure 4:
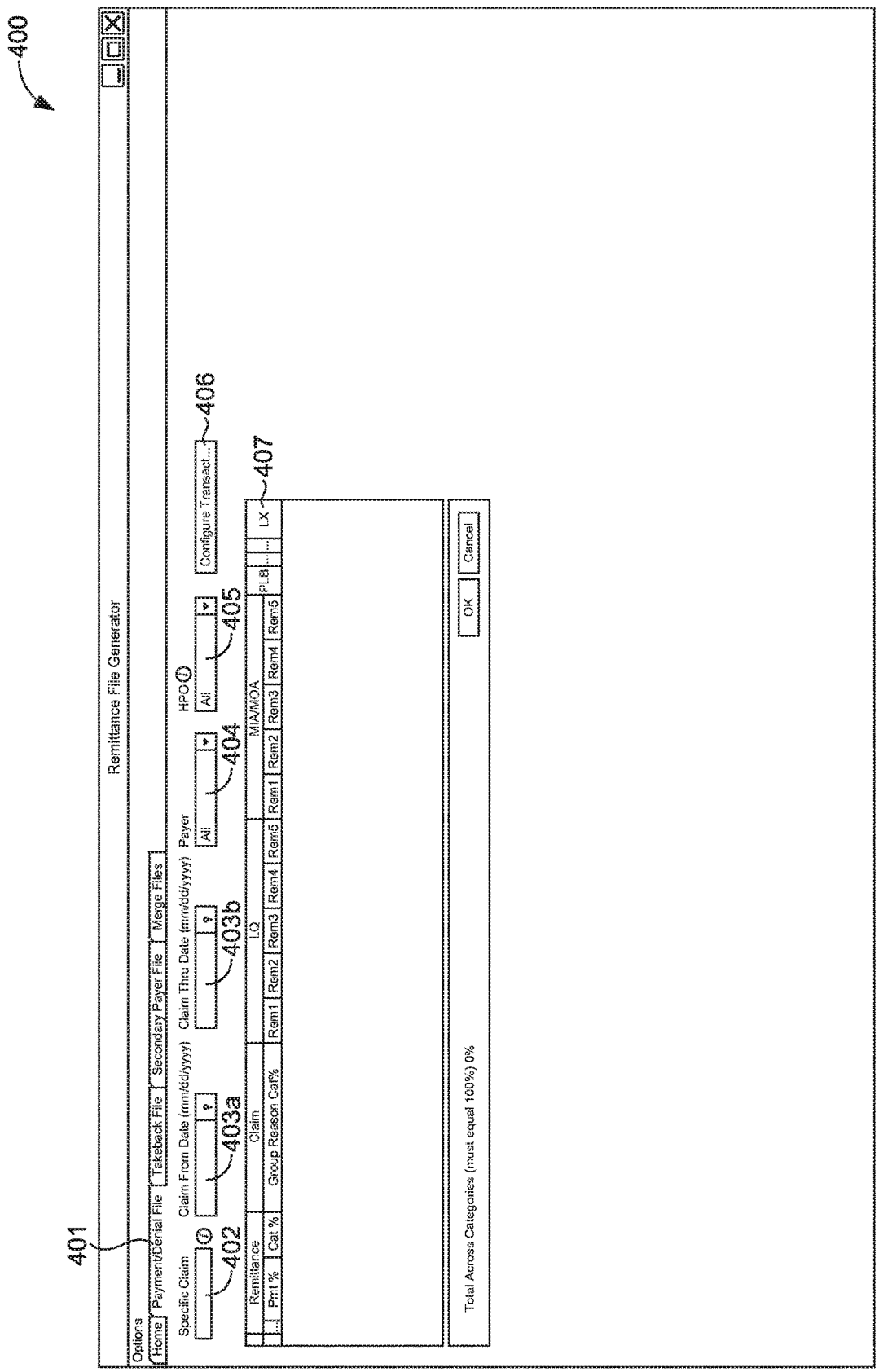

FIG. 4 provides an exemplary interface 400 showing a payment/denial file type selection (shown as reference numeral 202 in FIG. 1). A specific claim identified may be input at claim input area 402. Alternatively, a date range for claims may be specified at range input areas 403*a* and 403*b*. The interface 400 also provides for claims information identification via a payer via payer input area 404 or a payee via payee input area 405. Once selected, the transaction can be configured upon selection of a configuration input 406. Appropriate configuration corresponding to the specified inputs may be provided in area 407.

Figure 5:
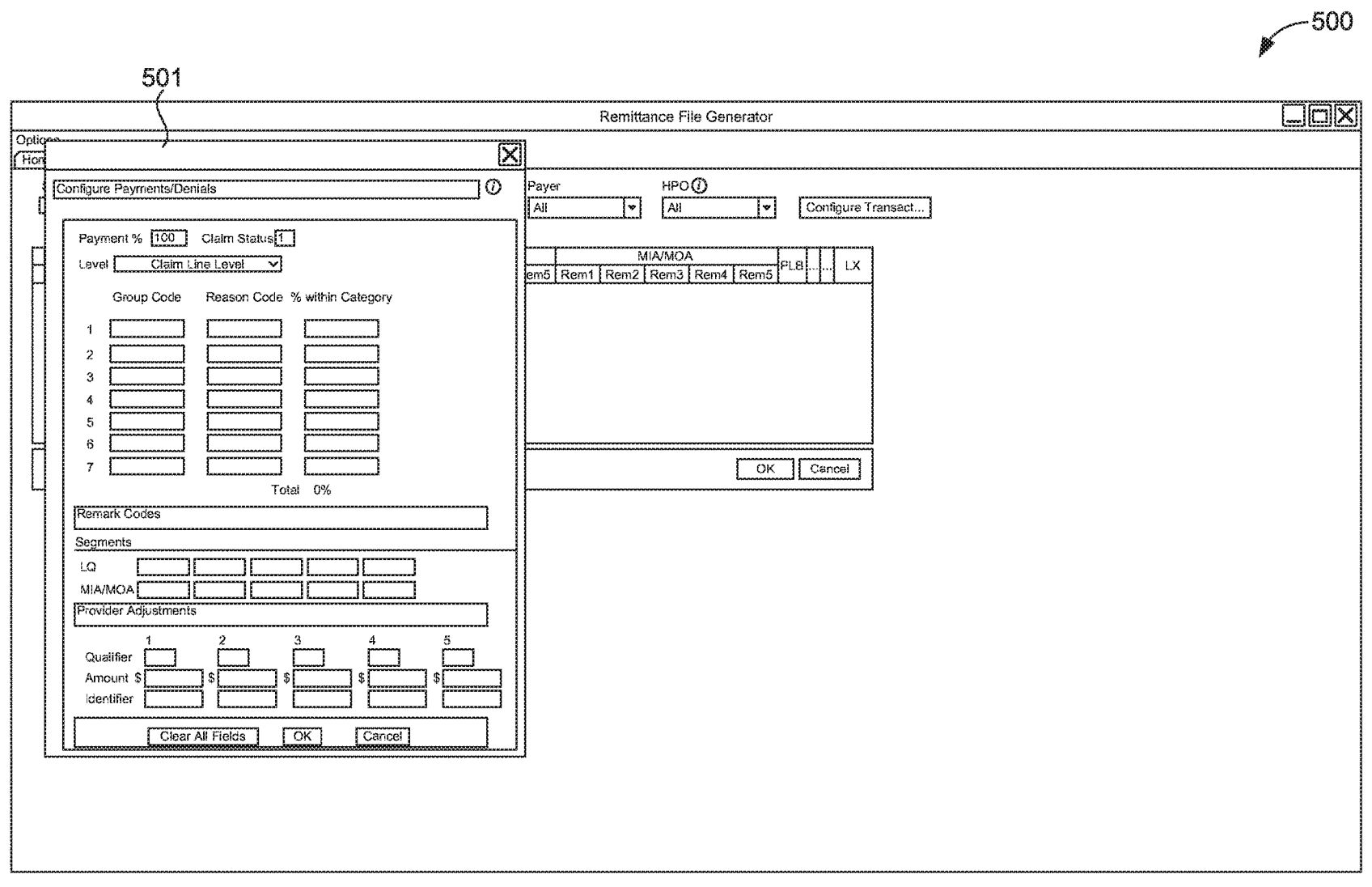

Upon selection of the configuration input 406, an interface 500 provided in FIG. 5 is presented. Here, test data, for example, may be input into the configuration dialog area 501 to configure a transmission. An expanded view is provided in FIG. 6 at interface 600. As shown, test data may be entered into area 601. Provider remarks may also be input at remark area 602. Provider adjustments may also be input at provider adjustment area 603. Unlike previous solutions, the present tool allows for inclusion of provider remarks and provider adjustments in the 835 transmission.

The inputs provided are included in an electronically generated 835 transmission. A user may, for instance, input specific test data here to trigger an existing rule to make sure the rule is performing properly. Once configured, the rules are generated as shown in interface 700 of FIG. 7. Area 701 includes configurations that will be utilized to populate 835 transmissions. Multiple configurations can be created to populate variations within one 835 transmission.

As shown, multiple configurations may be generated to allow for testing of different scenarios. Providers do not adjudicate everything the same so many different files may be desired to test many situations. Additionally, providers do not adjudicate a similar file from different entities the same. For instance, a provider may adjudicate a file from entity A one way but adjudicate a file from entity B differently. Rules can be built into the 835 transmission processing system to handle these different scenarios and the 835 transmission generator can test each one of them. Once the desired rules are populated, selection of the OK button navigates a user to a generation interface 800 shown in FIG. 8. Selection of the generation button 801 initiates generation of the 835 transmission(s).

Figure 9:
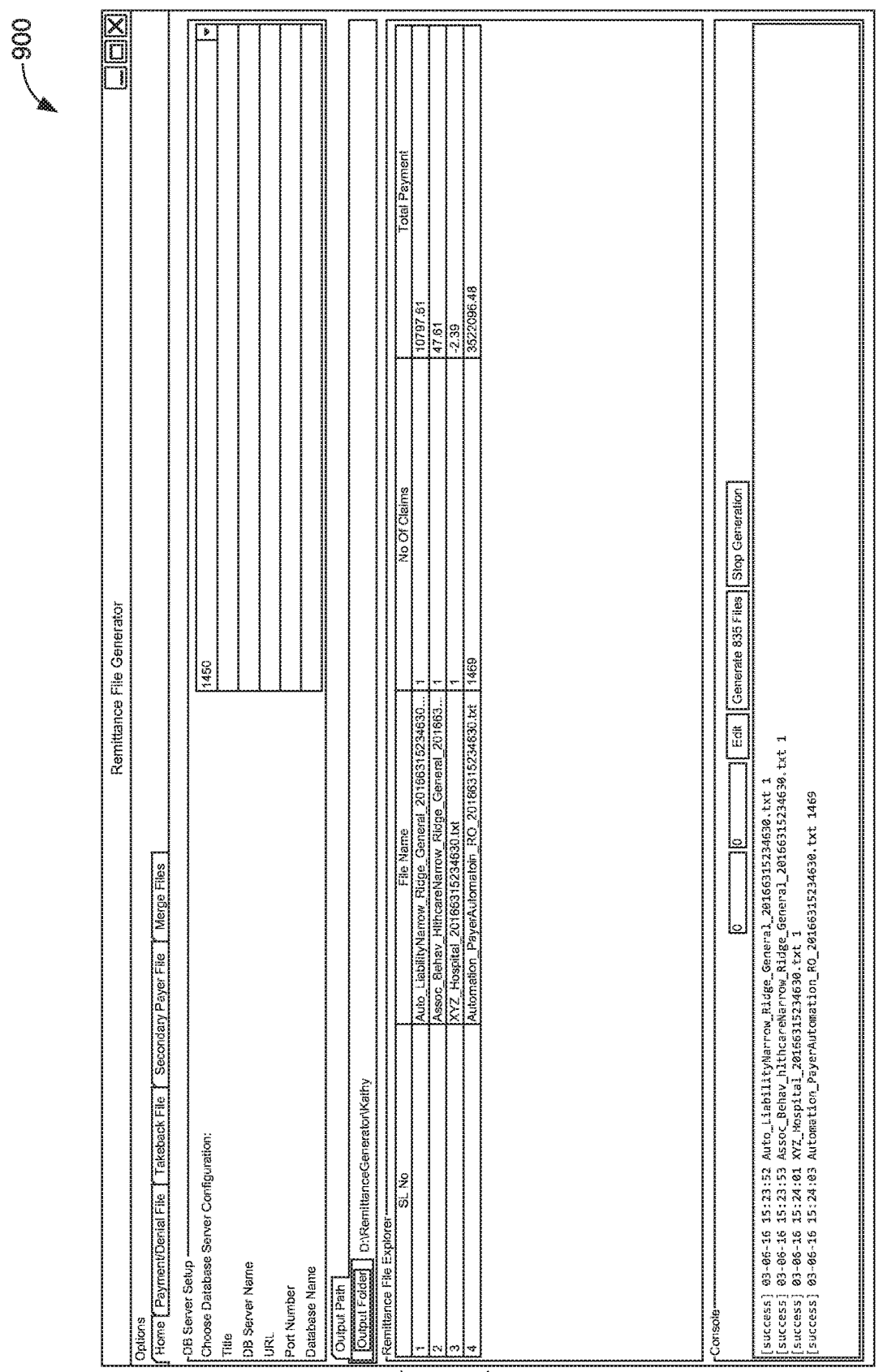
Figure 10:
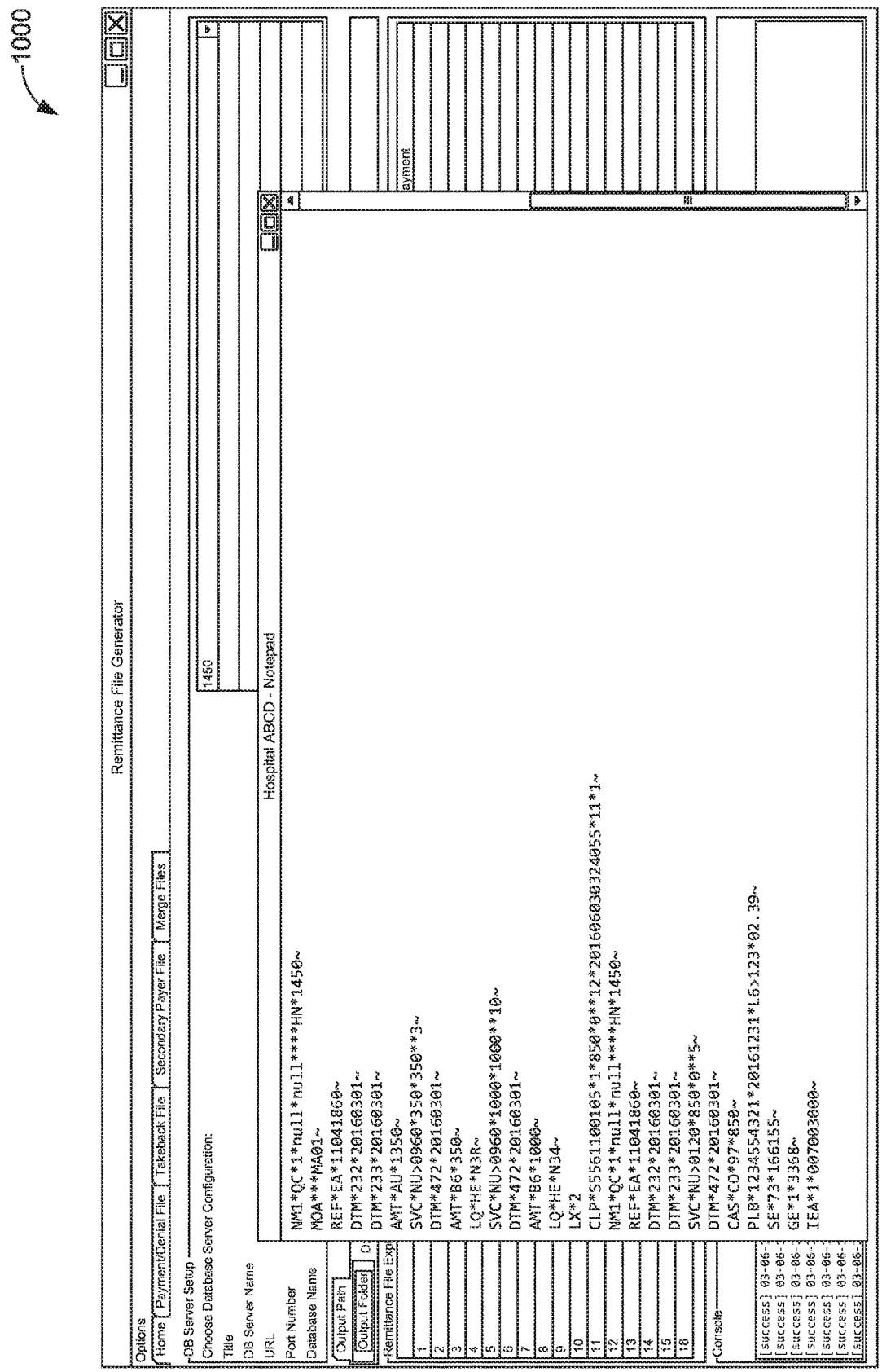

As shown in FIG. 9, the interface 900 includes the generated files the user requests. The files may be opened to view the 835 transmission (shown in interface 1000 of FIG. 10). As shown in FIG. 10, the generated transmissions include the info that was input. The tool allows you to include remark codes and provider adjustment segments and uses the database to fill in the claims information (provider information, claim number, insurance policy number, medical record number, dates of service, allowed amounts, etc.).

Figure 11:
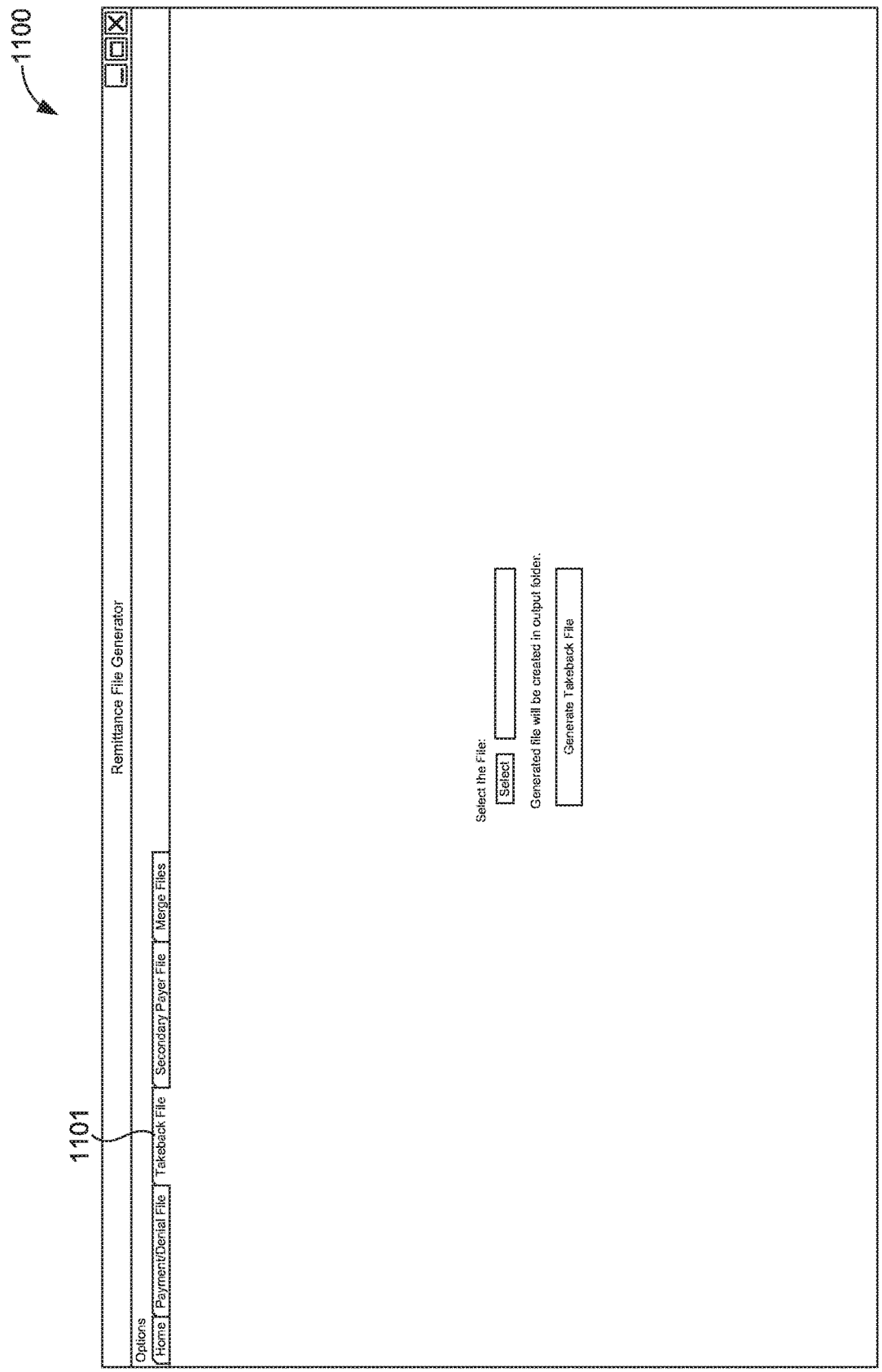
Figure 12:
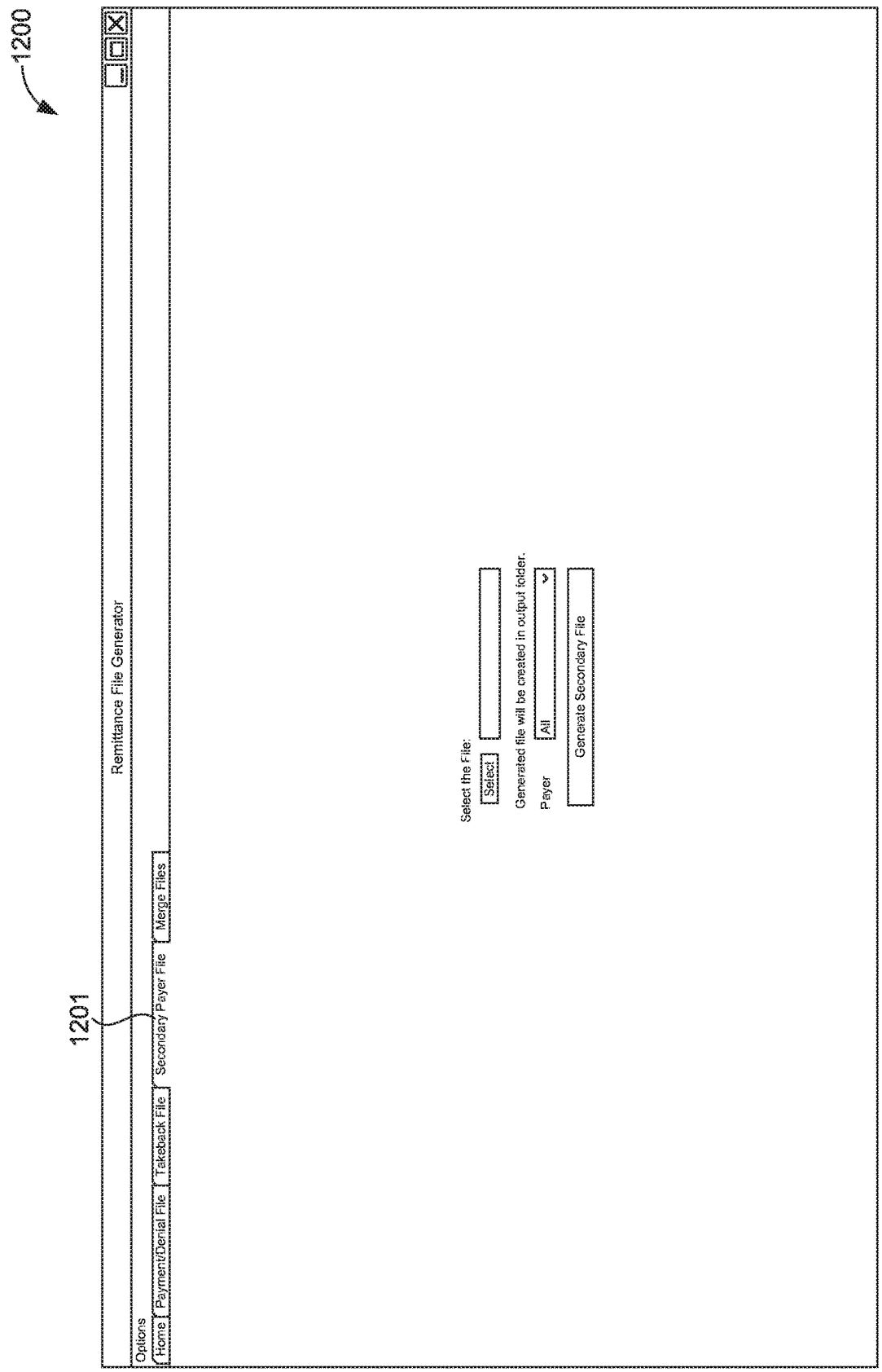

FIGS. 11 and 12 illustrate interfaces 1100 and 1200 showing takeback file generation selections 1101 and secondary/payer file selections 1201. These files utilize an existing 835 transmission to create the takeback and secondary files.

FIG. 13 provides an exemplary system interface 1300 showing one or more rule sets that may be written into the 835 processing system. These are, for example, some of the rules a user would like to test. Rule sets may be selected from a rule sets area 1301 to show individual rules within the rule set. The individual rules are provided in rules area 1302. Selection of a rule may result in an explanation or additional detail of the rule to be provided.

Figure 6:
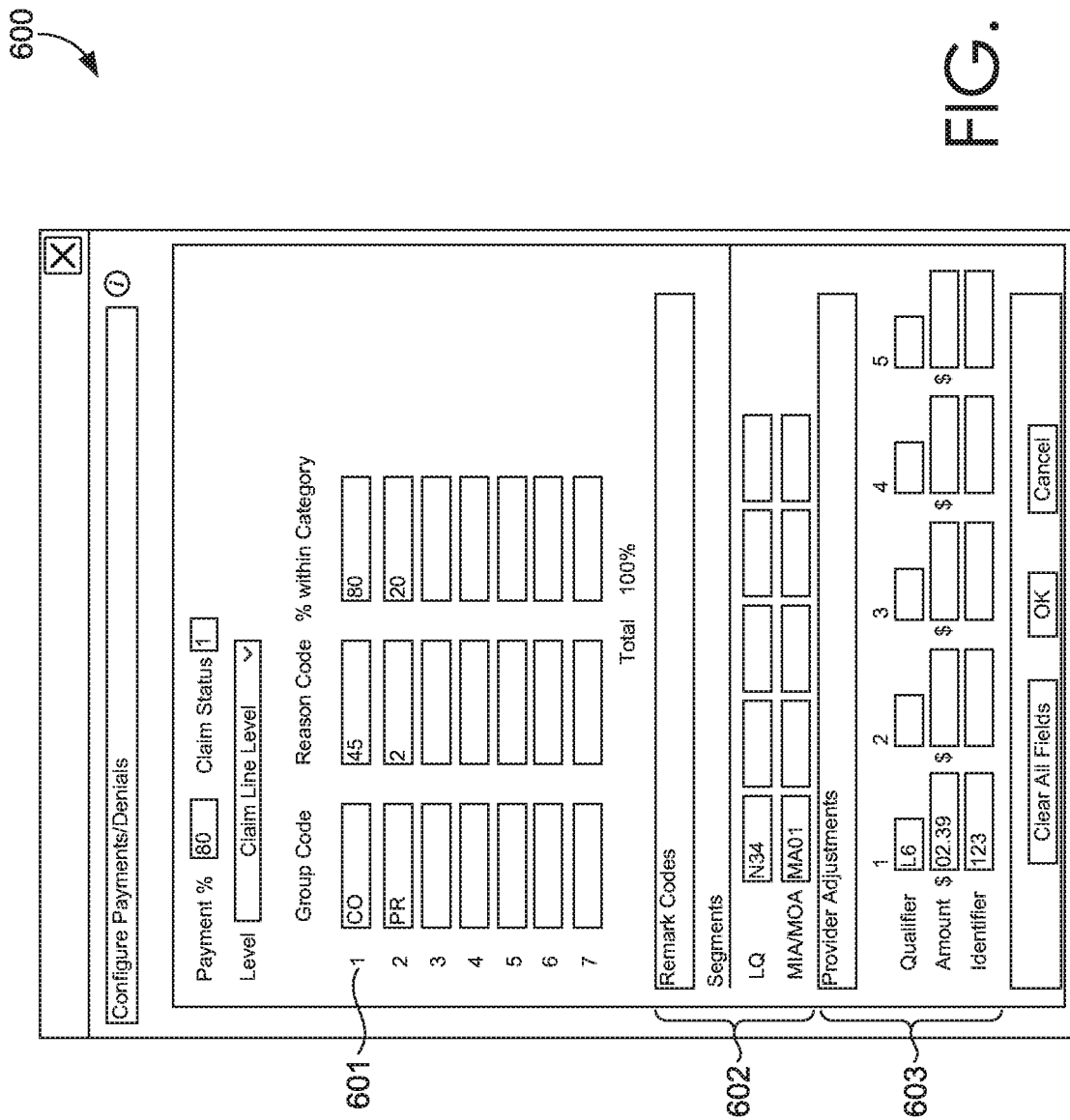
Figure 14:
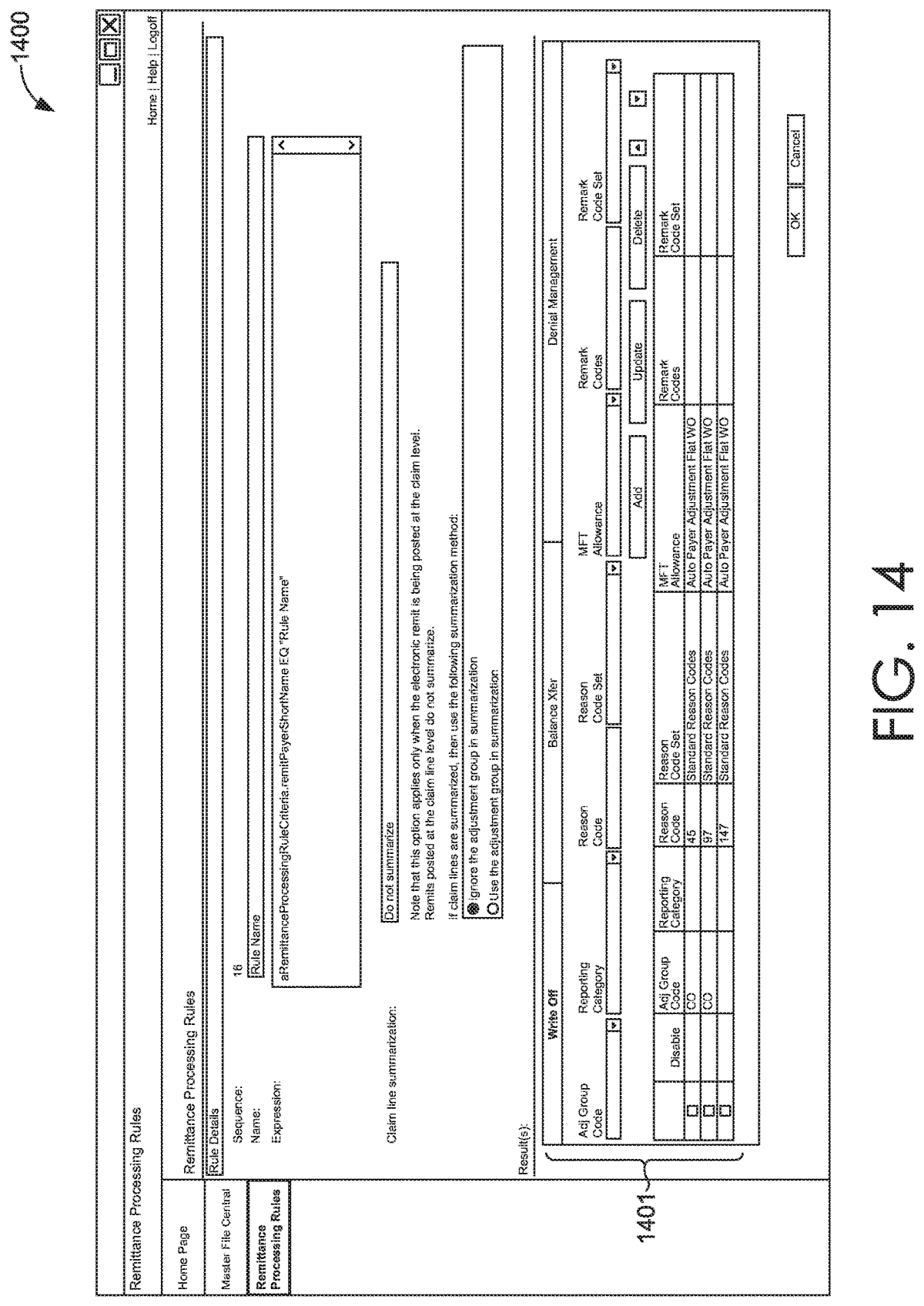

FIG. 14 provides an additional exemplary interface 1400 showing specific rules to test. Note that one of the rules has an "Adj. Group Code" of "CO" and a reason code of "45". "CO 45" was input into the 835 transmission to test this rule as shown in FIG. 6 (numeral 601). FIG. 15 also provides a view 1500 of a generated transmission including the "CO 45" test input 1501. Thus, a user can expect that the generated transmission including the "CO 45" test input will be handled a certain way pursuant to the rules of the system. If so, that rule has been successfully testing for implementation. If not, it will be easy to detect there is a problem to address. In this instance, the tool provides for iterative processing capabilities to re-process the 835 transmission until the problem is addressed.

Additionally, as previously mentioned, the tool has the ability to merge files to test multiple data sets at once. Selection of the button indicated at numeral 205 of FIG. 2 provides a merge option. Multiple files may be merged together and the files may be of different types. For instance, a payment and secondary payment file type can be merged into one file. Additionally, payment files and takeback files may also be merged together. Any types of files can be merged into a single file. Every file has a unique header unique to that file and there can only be one set of headers in an 835 transmission. Thus, the 835 transmission generator extracts header information from each of the files to be merged and translates the information into a merged header that represents each of the merged files.

Once files are merged, a total number of lines and check amount is recalculated by the tool. For example, each of the files merged included a total number of lines of that file but when it was combined with other files, the merged transmission has a different number of lines than each of the files combined therein. Thus, the total number of lines is recalculated and included in the transmission data. A similar process is followed for check amount where payments amounts from each file are combined and included in the transmission data.

Figure 16:
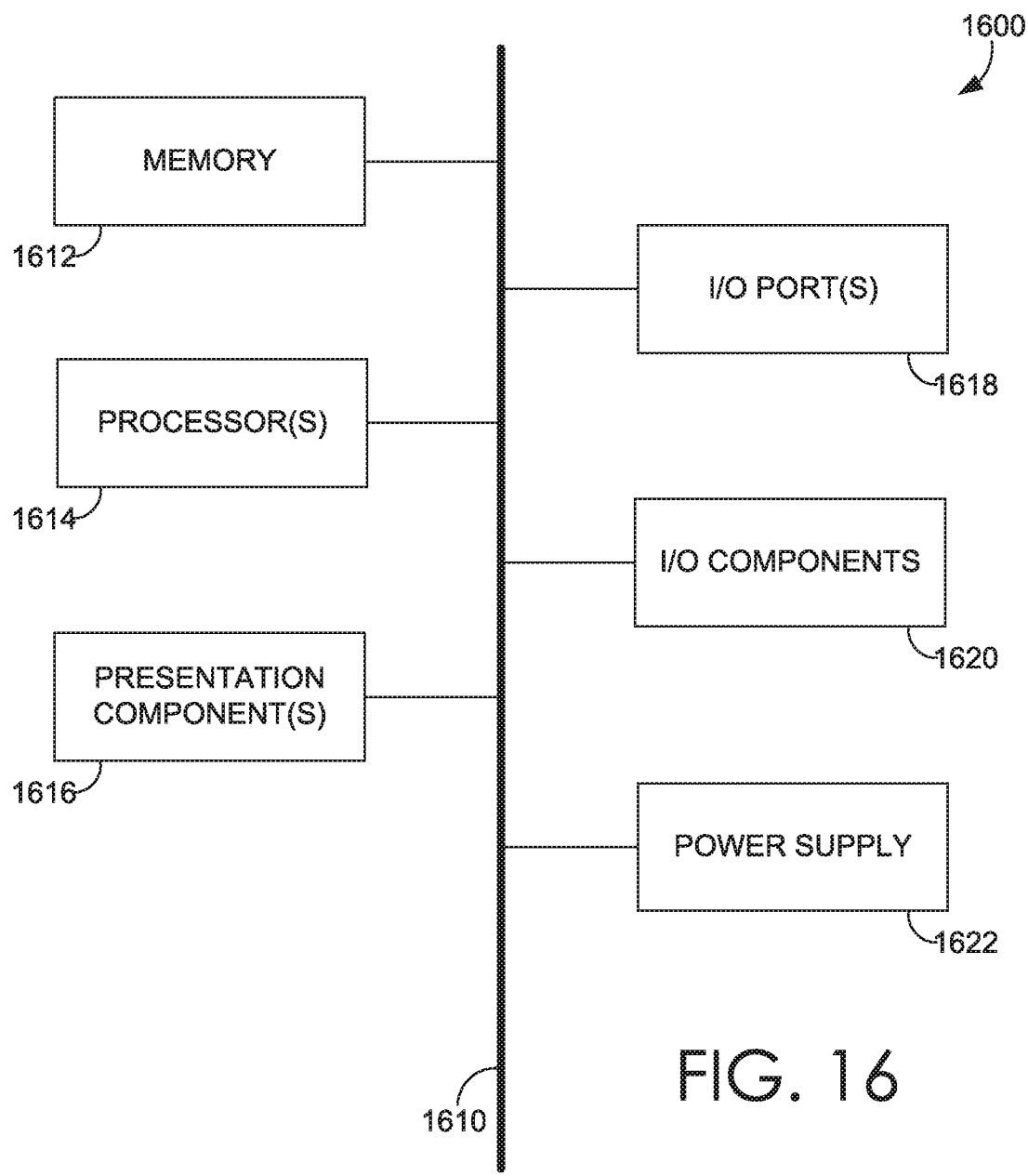
FIG. 16 is a block diagram of an exemplary computing environment suitable for use in implementations of the present disclosure.

Having described implementations of the present disclosure, an exemplary operating environment in which embodiments of the present invention may be implemented is described below in order to provide a general context for various aspects of the present disclosure. Referring to FIG. 16 in particular, an exemplary operating environment for implementing embodiments of the present invention is shown and designated generally as computing device 1600. Computing device 1600 is but one example of a suitable computing environment and is not intended to suggest any limitation as to the scope of use or functionality of the invention. Neither should the computing device 1600 be interpreted as having any dependency or requirement relating to any one or combination of components illustrated.

The invention may be described in the general context of computer code or machine-useable instructions, including computer-executable instructions such as program modules, being executed by a computer or other machine, such as a personal data assistant or other handheld device. Generally, program modules including routines, programs, objects, components, data structures, etc., refer to code that perform particular tasks or implement particular abstract data types. The invention may be practiced in a variety of system configurations, including hand-held devices, consumer electronics, general-purpose computers, more specialty computing devices, etc. The invention may also be practiced in distributed computing environments where tasks are performed by remote-processing devices that are linked through a communications network.

With reference to FIG. 16, computing device 1600 includes bus 1610 that directly or indirectly couples the following devices: memory 1612, one or more processors 1614, one or more presentation components 1616, input/output (I/O) ports 1618, input/output components 1620, and illustrative power supply 1622. Bus 1610 represents what may be one or more busses (such as an address bus, data bus, or combination thereof). Although the various blocks of FIG. 16 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventors recognize that such is the nature of the art, and reiterate that the diagram of FIG. 16 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 16 and reference to "computing device."

Computing device 1600 typically includes a variety of computer-readable media. Computer-readable media can be any available media that can be accessed by computing device 1600 and includes both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 1600. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 1612 includes computer storage media in the form of volatile and/or nonvolatile memory. The memory may be removable, non-removable, or a combination thereof. Exemplary hardware devices include solid-state memory, hard drives, optical-disc drives, etc. Computing device 1600 includes one or more processors that read data from various entities such as memory 1612 or I/O components 1620. Presentation component(s) 1616 present data indications to a user or other device. Exemplary presentation components include a display device, speaker, printing component, vibrating component, etc.

I/O ports 1618 allow computing device 1600 to be logically coupled to other devices including I/O components 1620, some of which may be built in. Illustrative components include a microphone, joystick, game pad, satellite dish, scanner, printer, wireless device, etc. The I/O components 1620 may provide a natural user interface (NUI) that processes air gestures, voice, or other physiological inputs generated by a user. In some instance, inputs may be transmitted to an appropriate network element for further processing. A NUI may implement any combination of speech recognition, touch and stylus recognition, facial recognition, biometric recognition, gesture recognition both on screen and adjacent to the screen, air gestures, head and eye-tracking, and touch recognition associated with displays on the computing device 1600. The computing device 1600 may be equipped with depth cameras, such as, stereoscopic camera systems, infrared camera systems, RGB camera systems, and combinations of these for gesture detection and recognition. Additionally, the computing device 1600 may be equipped with accelerometers or gyroscopes that enable detection of motion.

As described above, implementations of the present disclosure relate to a design tool that facilitates generating user interface code for applications. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. One or more non-transitory computer storage media storing computer-useable instructions that, when executed by a computing device, cause the computing device to perform operations, the operations comprising:
    detecting an indication of a database that stores a plurality of actual claims that have been submitted for reimbursement;
    detecting an indication of a configuration input that defines one or more of a claim type, a claim date range, payer information, or payee information to be extracted from the database;
    extracting claims data that corresponds to the one or more of the claim type, the claim date range, the payer information, or the payee information defined by the configuration input, the claims data being extracted from the plurality of actual claims that have been submitted for reimbursement and are stored in the database;
    detecting test data;
    electronically generating a plurality of Electronic Data Interchange (EDI) 835 transmissions by formatting the claims data extracted into a predetermined format and by inserting the test data detected;
    determining a size capability of an 835 processing system by using the test data from the plurality of EDI 835 transmissions generated; and
    based on the size capability, providing an indication of an area to increase a processing power of the 835 processing system.

2. The one or more computer storage media of claim 1, wherein the test data includes implementation adjustment data, and wherein the size capability of the 835 processing system is determined based on a number of lines corresponding to files associated with the claims data.

3. The one or more computer storage media of claim 1, wherein the plurality of EDI 835 transmissions includes one or more provider remarks related to a corresponding EDI 835 transmission, wherein the one or more provider remarks are included in the test data and included in the plurality of EDI 835 transmissions.

4. The one or more computer storage media of claim 1, wherein the test data includes copay data, and wherein the operations further comprise:
    merging files corresponding to the claims data;
    determining a number of lines corresponding to the merged files; and
    providing the indication based on the number of lines.

5. The one or more computer storage media of claim 1, wherein the claims data extracted includes two or more of: the claim date range, a service rendered, the payer information, provider information, and a code corresponding to the service rendered.

6. The one or more computer storage media of claim 1, wherein the test data corresponds to one or more rules for handling EDI 835 transmissions.

7. A computer-implemented method for electronically generating EDI 835 transmissions, the method comprising:
detecting (1) a selection of a database that stores a plurality of submitted claims, (2) test data, and a configuration input that defines one or more of a claim type, a claim date range, payer information, or payee information to be extracted;
extracting, from a first and second claim of the plurality of submitted claims stored in the database, claims information that corresponds to the one or more of the claim type, the claim date range, the payer information, or the payee information defined by the configuration input;
generating a first EDI 835 transmission by formatting the claims information extracted from the first claim and inserting the test data;
generating a second EDI 835 transmission by formatting the claims information extracted from the second claim and inserting the test data;
generating a third EDI 835 transmission by merging the first and second EDI 835 transmission together, wherein the third EDI 835 transmission is formatted to a predetermined format;
determining a size capability of an 835 processing system by using the test data from the third EDI 835 transmission; and
based on the size capability, providing an indication of an area to increase a processing power of the 835 processing system.

8. The method of claim 7, wherein the first EDI 835 transmission is a first transmission type and the second EDI 835 transmission is a second transmission type, wherein the first transmission type is different from the second transmission type, and wherein the third EDI 835 transmission is generated to include the first and second transmission types.

9. The method of claim 8, wherein the first or the second transmission type includes a payment transmission type, and wherein the size capability of the 835 processing system is determined based on a number of lines corresponding to a file associated with the test data from the third EDI 835 transmission.

10. The method of claim 9, wherein the method further comprises:
extracting header information from the first EDI 835 transmission and the second EDI 835 transmission.

11. The method of claim 10, wherein the method further comprises:
translating the header information from the first EDI 835 transmission and the second EDI 835 transmission to create a merged header for the third EDI 835 transmission.

12. The method of claim 11, wherein the method further comprises:
calculating a total number of lines and payment amounts in the third EDI 835 transmission, wherein the total number of lines is an aggregation of a plurality of lines from the first EDI 835 transmission with a plurality of lines from the second EDI 835 transmission.

13. A computer system comprising:
one or more processors; and
one or more computer storage media storing computer-useable instructions that, when used by the one or more processors, cause the one or more processors to:
detect (1) a selection of a database that stores a plurality of submitted claims, (2) test data, and (3) a configuration input that defines one or more of a claim type, a claim date range, payer information, or payee information to be extracted;
extract, from a first claims and a second claim in the plurality of submitted claims stored in the database, claims information that corresponds to the one or more of the claim type, the claim date range, the payer information, or the payee information defined by the configuration input;
generate a first EDI 835 transmission by formatting the claims information from the first claim and inserting the test data;
generate a second EDI 835 transmission by formatting the claims information from the second claim and inserting the test data;
generate a third EDI 835 transmission by merging the first and second EDI 835 transmission together, wherein the third EDI 835 transmission is formatted to a predetermined format;
determine a size capability of an 835 processing system by using the test data from the third EDI 835 transmission; and
based on the size capability, provide an indication of an area to increase a processing power of the 835 processing system.

14. The system of claim 13, wherein the first EDI 35 transmission is a first transmission type and the second EDI 835 transmission is a second transmission type; and wherein the size capability of the 835 processing system is determined based on a number of lines corresponding to a file associated with the test data from the third EDI 835 transmission.

15. The system of claim 14, wherein the first transmission type is different from the second transmission type, and wherein the third EDI 835 transmission is generated to include the first and second transmission types.

16. The system of claim 15, wherein the instructions further cause the one or more processors to:
extract header information from the first EDI 835 transmission and the second EDI 835 transmission.

17. The system of claim 16, wherein the instructions further cause the one or more processors to:
translate the header information from the first EDI 835 transmission and the second EDI 835 transmission to create a merged header for the third EDI 835 transmission.

18. The system of claim 17, wherein the instructions further cause the one or more processors to:
calculate a total number of lines in the third EDI 835 transmission.

19. The method of claim 7, further comprising:
testing, using the third EDI 835 transmission, a performance of the 835 processing system using a rule set of the test data prior to a live implementation; and
implementing the 835 processing system.

* * * * *

UNITED STATES PATENT AND TRADEMARK OFFICE
CERTIFICATE OF CORRECTION

PATENT NO. : 11,309,075 B2
APPLICATION NO. : 15/393671
DATED : April 19, 2022
INVENTOR(S) : Anthony et al.

It is certified that error appears in the above-identified patent and that said Letters Patent is hereby corrected as shown below:

In the Claims

Column 10, Line 34 In Claim 14, delete "35" and insert -- 835 --.

Signed and Sealed this
Thirty-first Day of May, 2022

Katherine Kelly Vidal
*Director of the United States Patent and Trademark Office*